United States Patent
Lu et al.

(10) Patent No.: US 10,509,021 B2
(45) Date of Patent: Dec. 17, 2019

(54) DIAGNOSING DEVICE FOR ON-LOAD TAP CHANGING APPARATUS, DIAGNOSING METHOD FOR ON-LOAD TAP CHANGING APPARATUS, AND DIAGNOSING DEVICE FOR TRANSFORMER

(71) Applicant: Hitachi, Ltd., Chiyoda-ku, Tokyo (JP)

(72) Inventors: Li Lu, Tokyo (JP); Yoshio Hamadate, Tokyo (JP); Toshiaki Rokunohe, Tokyo (JP); Akira Yamagishi, Tokyo (JP); Hideyuki Miyahara, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 16/130,308

(22) Filed: Sep. 13, 2018

(65) Prior Publication Data

US 2019/0101521 A1  Apr. 4, 2019

(30) Foreign Application Priority Data

Oct. 4, 2017  (JP) ................................ 2017-194204

(51) Int. Cl.
*G01N 33/28* (2006.01)
*H01F 27/28* (2006.01)
*G01N 21/25* (2006.01)

(52) U.S. Cl.
CPC ......... *G01N 33/2888* (2013.01); *G01N 21/25* (2013.01); *H01F 27/28* (2013.01)

(58) Field of Classification Search
CPC ..... G01N 33/2888; G01N 21/25; H01F 27/28
USPC .......................................................... 356/70
See application file for complete search history.

(56) References Cited

U.S. PATENT DOCUMENTS

| | | | | |
|---|---|---|---|---|
| 3,662,253 | A * | 5/1972 | Yamamoto | H01F 29/04 323/343 |
| 5,774,228 | A | 6/1998 | Takezawa et al. | |
| 6,459,995 | B1 * | 10/2002 | Collister | G01N 27/221 702/104 |
| 6,476,396 | B1 * | 11/2002 | Forsyth | G01J 1/42 250/372 |
| 2014/0265635 | A1 * | 9/2014 | Lefeber | G01R 31/3274 307/117 |

(Continued)

FOREIGN PATENT DOCUMENTS

JP          10-74628 A          3/1998

*Primary Examiner* — Roy M Punnoose
(74) *Attorney, Agent, or Firm* — Crowell & Moring LLP

(57) ABSTRACT

There is provided a diagnosing device for an on-load tap changing apparatus of a transformer, which can diagnose the degradation degree of insulating oil at high accuracy by a relatively simple device configuration. A diagnosing device for an on-load tap changing apparatus has an insulating oil tank in which insulating oil is sealed, a changeover switching device that is disposed within the insulating oil tank and performs the tap changing operation of a tap winding, a tap selector that selects the tap position of the tap winding, and a polarity (transposition) changer that inverts the polarity of the tap winding or a winding connected to the tap winding. The diagnosing device includes an arc discharge light detector that detects arc discharge light that is emitted at changing the tap position of the tap selector. The degradation degree of the insulating oil is diagnosed based on the arc discharge light detected by the arc discharge light detector.

18 Claims, 5 Drawing Sheets

(56) References Cited

U.S. PATENT DOCUMENTS

2016/0018840 A1* 1/2016 Strof .................. G05F 5/00
                                                                                 323/301

\* cited by examiner

DIAGNOSING DEVICE FOR ON-LOAD TAP CHANGING APPARATUS, DIAGNOSING METHOD FOR ON-LOAD TAP CHANGING APPARATUS, AND DIAGNOSING DEVICE FOR TRANSFORMER

BACKGROUND

The present invention relates to an on-load tap changing apparatus of a transformer. More specifically, the present invention relates to a technique effective in being applied to the diagnosis of the degradation degree of insulating oil in a mechanical on-load tap changing apparatus.

An on-load tap changing apparatus is disposed in a transformer of an electric power transmission and distribution system. When the load of the electric power transmission and distribution system fluctuates and the change in voltage due to this fluctuation exceeds a fixed limit, the tap of the on-load tap changing apparatus disposed in the transformer is changed to keep the voltage of the electric power transmission and distribution system constant. The on-load tap changing apparatus includes a changing signal generation unit, an on-load tap changer, and an electrically driven operation mechanism, the on-load tap changer further including a changeover switching device and a tap selector (including a polarity changer or a transposition changer).

The outline of the changing operation of the on-load tap changing apparatus having such a configuration is as follows. That is, when the change in voltage exceeds the fixed limit, a signal is first created in the changing signal generation unit, so that the electrically driven operation mechanism is started to drive the on-load tap changer. As a result, the drive shaft of the on-load tap changer rotates, so that by the drive force of the drive shaft, the movable contact of the tap selector is disconnected and moved from one fixed contact, and is thrown into another fixed contact. In response to this, the changeover switching device performs the changing operation from one tap to another tap.

During the operation of the movable contact by the changeover switching device or at changing the tap of the tap selector, arc discharge occurs. This degrades insulating oil within the on-load tap changing apparatus, and in some cases, the internal device results in dielectric breakdown. On the other hand, likewise, discharge occurs in the tap selector and the polarity (transposition) changer.

In the conventional on-load tap changing apparatus configured as described above, in particular, when a fault is caused in the on-load tap changing apparatus of the electric power transmission and distribution system that serves as a main trunk line, the possibility of power failure over a wide range is high, which is a problem. Consequently, to prevent various faults, the maintaining and inspecting operation for the configuring devices and the configuring members is necessary. For this, the cover of the tap changing apparatus is opened periodically to evaluate the degradation degree of insulating oil by using oil extraction analysis by extracting the insulating oil. When the degradation degree progresses, the insulating oil is replaced.

As the diagnosing method for estimating the degradation degree and the life of insulating oil or insulating paper in an oil-immersed electric apparatus, a method by which, typically, furfural, carbon monoxide, carbon dioxide, and the like that are the decomposition products of the insulating paper are extracted from the insulating oil, and are subjected to gas analysis, thereby estimating the degradation degree from a separately determined correlation chart between the amount of gas generated and the polarization residual rate of the insulating paper, and the like are proposed. However, the above conventional technique is not a simple diagnosing method from the reasons of the request for special means that extracts, from the oil, a very small amount of gas generated with degradation, the large-sized evaluation apparatus for gas analysis, and the like.

As the background art of this technical field, for example, there is a technique as disclosed in Japanese Unexamined Patent Application Publication No. Hei10(1998)-74628. Japanese Unexamined Patent Application Publication No. Hei10(1998)-74628 discloses "A method by which a light source including at least two monochromatic light sources having wavelengths different from each other or a halogen lamp that emits white continuous light is provided, the irradiation light from the light source is spectrally dispersed through a spectroscope to at least two monochromatic lights having wavelengths different from each other, the at least two monochromatic irradiation lights that have been created in this manner are transmitted into an insulating medium, reflection light-absorption degrees ($A\lambda$) at the respective wavelengths of the obtained lights are calculated, a reflection light-absorption degree difference ($\Delta A\lambda$) or a reflection light-absorption degree ratio ($A\lambda'$) between the two wavelengths is calculated, the relation (master curve) between the degradation degree of a material to be measured and the reflection light-absorption degree difference or the reflection light-absorption degree ratio is previously determined, and at measuring the degradation degree of the material to be measured, the obtained reflection lights are used to be subjected to comparison computation with the obtained master curve to determine the degradation degree.

SUMMARY

In the method of Japanese Unexamined Patent Application Publication No. Hei10(1998)-74628, when the degradation degree of the insulator is diagnosed, the at least two monochromatic light sources having wavelengths different from each other are required to be used. In addition, to obtain the reflection light-absorption degree difference or the reflection light-absorption degree ratio, which is the fixed value with respect to the insulating oil having the same degradation degree, the light source intensities of the two monochromatic light sources are required to be adjusted in light amount so that the intensities in the light amount measurement unit are the fixed value. The intensity correction is always required with the degradation of the light source, which is very troublesome. In addition, when the white continuous light is used, the white continuous light is required to be spectrally dispersed through the spectroscope to the at least two monochromatic lights having wavelengths different from each other, resulting in the device becoming complicated.

Accordingly, an object of the present invention is to provide a diagnosing device for an on-load tap changing apparatus of a transformer, which can diagnose the degradation degree of insulating oil at high accuracy by a relatively simple device configuration.

In addition, another object of the present invention is to provide a diagnosing method for an on-load tap changing apparatus of a transformer, which can diagnose the degradation degree of insulating oil at high accuracy by a relatively simple method.

To solve the above problems, the present invention provides a diagnosing device for an on-load tap changing apparatus having an insulating oil tank in which insulating oil is sealed, a changeover switching device that is disposed within the insulating oil tank and performs the tap changing operation of a tap winding, a tap selector that selects the tap position of the tap winding, and a polarity (transposition) changer that inverts the polarity of the tap winding or a winding connected to the tap winding. The diagnosing device includes an arc discharge light detector that detects arc discharge light that is emitted at changing the tap position of the tap selector. The degradation degree of the insulating oil is diagnosed based on the arc discharge light detected by the arc discharge light detector.

Also, the present invention provides a diagnosing method for an on-load tap changing apparatus having an insulating oil tank in which insulating oil is sealed, a changeover switching device that is disposed within the insulating oil tank and performs the tap changing operation of a tap winding, a tap selector that selects the tap position of the tap winding, and a polarity (transposition) changer that inverts the polarity of the tap winding or a winding connected to the tap winding. Arc discharge light that is emitted at changing the tap position of the tap selector is received by a light reception unit. The arc discharge light detected by the light reception unit is transferred through an optical fiber to detection units that are disposed on the outside of the insulating oil tank. The arc discharge light is subjected to computation processing by a signal processing unit based on the wavelength and the intensity of the arc discharge light detected by the detection units to diagnose the degradation degree of the insulating oil.

Also, the present invention provides a diagnosing device for a transformer having a transformer tank in which insulating oil is sealed, and an on-load tap changing apparatus that is disposed within the transformer tank. The on-load tap changing apparatus includes a changeover switching device that performs the tap changing operation of a tap winding, a tap selector that selects the tap position of the tap winding, and a polarity (transposition) changer that inverts the polarity of the tap winding or a winding connected to the tap winding. The transformer includes, within the transformer tank, an arc discharge light detector that detects arc discharge light that is emitted at changing the tap position of the tap selector. The degradation degree of the insulating oil is diagnosed based on the arc discharge light detected by the arc discharge light detector.

According to the present invention, it is possible to achieve the diagnosing device for the on-load tap changing apparatus of the transformer, which can diagnose the degradation degree of the insulating oil at high accuracy by a relatively simple device configuration.

Also, it is possible to achieve the diagnosing method for the on-load tap changing apparatus of the transformer, which can diagnose the degradation degree of the insulating oil at high accuracy by a relatively simple method.

Objects, configurations, and effects other than the above will be apparent from the description of the following embodiments.

DETAILED DESCRIPTION

Embodiments of the present invention will now be described with reference to the drawings. It should be noted that the same configurations are indicated by similar reference signs in the respective drawings, and the detailed description of overlapped portions is omitted.

First Embodiment

Referring to FIGS. 1 to 4, a diagnosing device and a diagnosing method for an on-load tap changing apparatus according to a first embodiment will be described.

Figure 1:
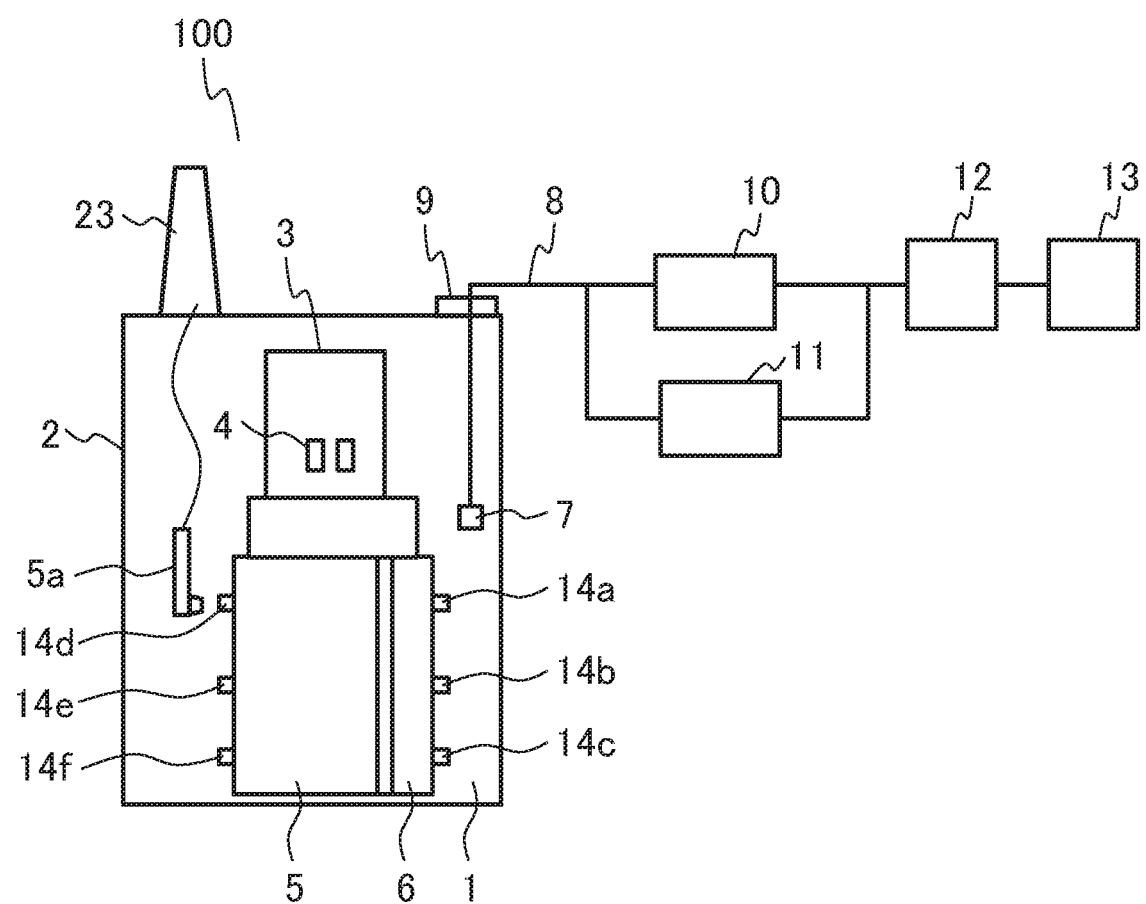
FIG. 1 is a diagram illustrating the overall outline of an on-load tap changing apparatus and a diagnosing device therefor according to an embodiment of the present invention (a first embodiment)
Figure 2:
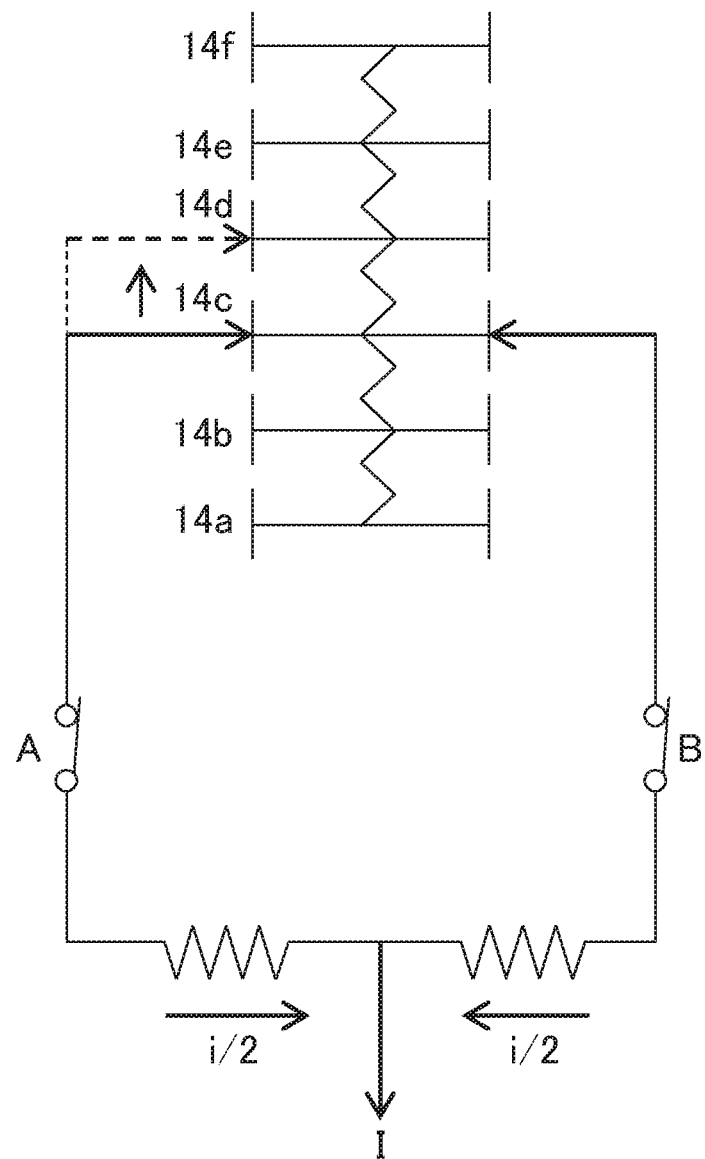
FIG. 2 is a diagram illustrating the principle of the tap position selection of the on-load tap changing apparatus according to an embodiment of the present invention.
Figure 3:
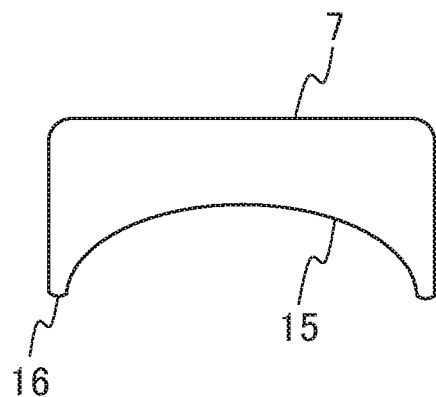
FIG. 3 is a diagram illustrating a light reception unit of the diagnosing device according to an embodiment of the present invention.
Figure 4:
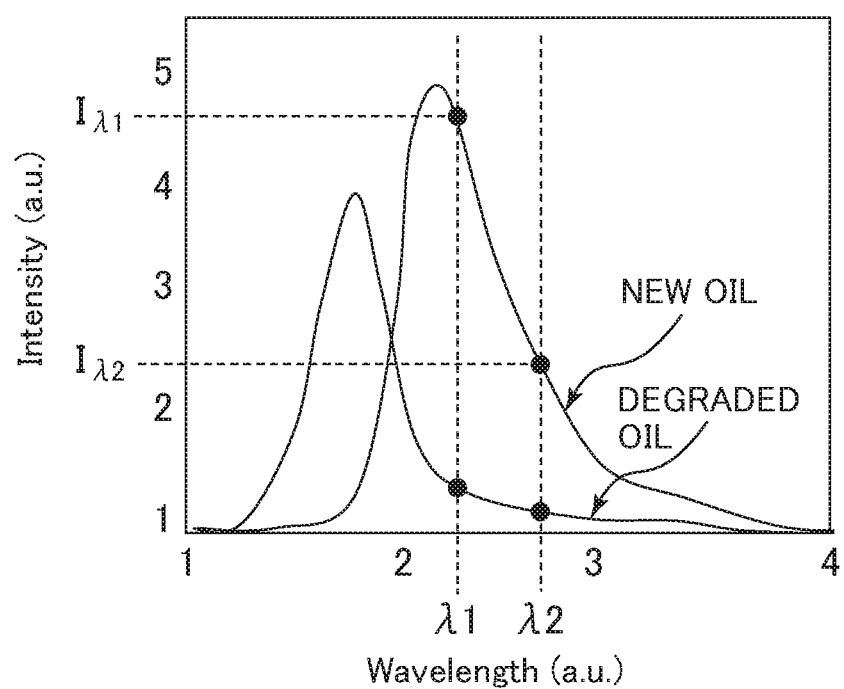
FIG. 4 is a chart illustrating spectral spectra obtained when arc discharge lights transmit through new oil and degraded oil of insulating oil.

FIG. 1 is a diagram illustrating the overall outline of the on-load tap changing apparatus and the diagnosing device therefor according to this embodiment. FIG. 2 is a diagram illustrating the principle of the tap position selection of the on-load tap changing apparatus. FIG. 3 is a partially enlarged sectional view of a light reception unit 7 in FIG. 1. FIG. 4 is a chart illustrating spectral spectra measured when incident lights including the wavelengths of arc discharge lights transmit through new oil and degraded oil of mineral oil that is a kind of insulating oil.

As illustrated in FIG. 1, an on-load tap changing apparatus 100 of this embodiment has a changeover switching device 3 that is disposed within an insulating oil tank 2 in which insulating oil 1 is sealed, a contact 4 that changes the tap in a state where a load is applied to the changeover switching device 3, that is, during electric conduction, a tap selector 5 that selects a tap position 14 (14a to 14f) of a tap winding, and a polarity (transposition) changer 6 that inverts the polarity of a winding.

The on-load tap changing apparatus 100 operates the changeover switching device 3 disposed in its interior, and changes the tap of the tap selector 5 in several stages to regulate the voltage. In addition, the polarity (transposition) changer 6 inverts the polarity of the tap winding or the winding connected to the tap winding in order to enlarge the regulation range of the voltage.

When the movable contact of the contact 4 that is disposed in the interior of the changeover switching device 3 moves from the fixed contact, arc discharge light is emitted. To prevent the arc discharge light, vacuum or the insulating oil is filled around the contact 4 in the interior of the changeover switching device 3. The arc discharge light is emitted light having very high intensity, so that at filling the insulating oil, the progressing speed of the degradation of the insulating oil becomes very high due to the influence of the arc discharge light.

On the other hand, the tap selector 5 that selects the tap position 14 (14a to 14f) in the tap currentless state of the tap winding and the polarity (transposition) changer 6 that inverts the polarity of the winding connected to the tap winding select the tap position in the currentless state, and likewise, arc discharge light occurs at changing the tap position. However, the intensity of the arc discharge light becomes lower than the intensity of arc discharge light that occurs at the movement of the movable contact of the contact 4 that is disposed in the interior of the changeover switching device 3.

The occurrence cause of arc discharge light when the tap position is selected by the tap selector 5 and the polarity (transposition) changer 6 will be described below by taking the operation of a reactor type on-load tap changing apparatus that is a kind of the on-load tap changing apparatus illustrated in FIG. 2, as an example.

As illustrated in FIG. 2, at the tap position 14c, changeover switches A and B are closed, and electric current having a magnitude that is half of load current i flows to the reactor in opposite directions, thereby canceling the respective reactances with each other. At moving to the tap position 14d, the changeover switch A is first opened to transfer the load current to the changeover switch B side, and next, the tap selector is moved to the predetermined tap position 14d. When the changeover switch A is closed, the voltage difference between the tap positions 14c and 14d is caused, and voltage having this voltage difference is applied onto the capacitance by the insulator, such as the insulating oil, between the tap positions 14c and 14d, so that arc discharge light occurs.

Thus, as illustrated in FIG. 1, in the on-load tap changing apparatus 100 of this embodiment, arc discharge light that occurs at changing the tap position is received by the light reception unit 7, the optical signal (arc discharge light) detected by the light reception unit 7 is transferred by using an optical fiber 8 through a hermetic terminal 9 mounted on the wall surface of the insulating oil tank 2 of the on-load tap changing apparatus 100, to a wavelength detection unit 10 and an intensity detection unit 11 that are disposed on the outside of the insulating oil tank 2 and detect the wavelength and the intensity of the arc discharge light, respectively, and the wavelength signal and the intensity signal are subjected to computation processing by a signal processing unit 12 to diagnose the degradation degree of the insulating oil 1 sealed in the insulating oil tank 2, so that the diagnostic result is displayed on a display unit 13.

It should be noted that more preferably, the light reception unit 7 for detecting the arc discharge light is disposed in the vicinity of the tap position of the tap selector 5 or the polarity (transposition) changer 6.

FIG. 3 is a partially enlarged sectional view illustrating the configuration of the light reception unit 7. In order that a larger amount of arc discharge light is received by the light reception unit, a light reception window 15 preferably has a large light reception surface, as illustrated in FIG. 3. For example, as illustrated in FIG. 3, the light reception surface is formed to be a recessed and circular surface. In addition, the light reception window 15 is preferably disposed so as to face (to be opposite) the tap position of the tap selector 5 or the polarity (transposition) changer 6.

To secure the insulation performance of the light reception unit 7 and the light reception window 15, an insulating material is desirably used. In addition, to prevent electric field concentration, curvature R of a corner 16 of the light reception unit 7 is desirably set to be a little too large dimension. For example, the curvature R is set to be larger than 10.

It should be noted that the signal of arc discharge light while being the optical signal is not processed by the monitoring devices (the wavelength detection unit 10 and the intensity detection unit 11). Thus, the optical signal is first converted to an electric signal through the converter, and is then amplified and analog-to-digital converted to be transferred to the wavelength detection unit 10 and the intensity detection unit 11.

For example, a signal processing technique for detecting the degradation degree of the insulating oil by using arc discharge light as a light source is as follows.

Typically, arc discharge light includes a wide wavelength range from the ultraviolet region to the infrared region. When the arc discharge light transmits through the same insulating oil, for example, new oil of mineral oil, the absolute intensity of the arc discharge light changes according to the changing voltage, but the intensity ratio with respect to the respective wavelengths is fixed.

On the other hand, the change in transmittance with respect to the respective wavelengths with the degradation of an organic material is represented by the change as illustrated in FIG. 4. FIG. 4 illustrates spectral spectra obtained when arc discharge lights transmit through new oil and degraded oil of the insulating oil. As illustrated in FIG. 4, when the degradation of the insulating oil progresses, the light intensity reduces. In addition, the peak value of the intensity tends to move to the short wavelength side. This is caused by the increase in electronic absorption loss from the thermal oxidation degradation reaction of the material due to arc discharge. In particular, the electronic absorption loss on the long wavelength side is significant.

Thus, at least two wavelengths $\lambda 1$ and $\lambda 2$ in which the wavelengths of arc discharge light received by the light reception unit 7 are different from each other are selected, and after transmission through the insulating oil, ratio $K=I_{\lambda 1}/I_{\lambda 2}$ of light intensities I at the wavelengths $\lambda 1$ and $\lambda 2$ is determined. Alternatively, intensity difference $\Delta I=I_{\lambda 1}-I_{\lambda 2}$ (where $\lambda 1<\lambda 2$) is determined.

As seen from FIG. 4, ratio $K=I_{\lambda 1}/I_{\lambda 2}$ or difference $\Delta I=I_{\lambda 1}-I_{\lambda 2}$ for the new oil and ratio $K=I_{\lambda 1}/I_{\lambda 2}$ or difference $\Delta I=I_{\lambda 1}-I_{\lambda 2}$ for the degraded oil are different. By using such a different characteristic, the degradation degree of the insulating oil is diagnosed.

The intensity ratio K or the intensity difference $\Delta I$ of the arc discharge light detected by the light reception unit 7 changes according to the degradation degree of the insulating oil, and hence, the relation (master curve) between the K or the $\Delta I$ and the insulating oil degradation degree is created, and is previously stored in the signal processing unit 12.

At diagnosing the degradation degree of the insulating oil, the intensity ratio K or the intensity difference $\Delta I$ of the detected arc discharge light is used to be subjected to comparison computation with the master curve stored in the signal processing unit 12, so that the degradation degree of the insulating oil can be determined.

As described above, in Japanese Unexamined Patent Application Publication No. Hei10(1998)-74628, the intensities of the irradiation lights from the light sources having the at least two wavelengths are required to be adjusted in light amount so that the intensities in the light amount measurement unit are the fixed value. On the contrary, in this embodiment, since arc discharge light is used as a light source, the intensities at the wavelengths $\lambda 1$ and $\lambda 2$ are fixed with respect to the same insulating oil, and thus, the trouble of the adjustment for always holding the irradiation intensities at the fixed ratio with respect to the incident light sources having two wavelengths can be reduced.

To create the correlation relation (master curve) between the intensity ratio K or the intensity difference $\Delta I$ of arc discharge light and the insulating oil degradation degree, actual arc discharge light and each of insulating oils having different degradation degrees can be used to measure the relation between the ratio K or the difference $\Delta I$ and the insulating oil degradation degree.

On the other hand, when there is no actual arc discharge light, monochromatic light having the two wavelengths $\lambda 1$ and $\lambda 2$ having the same intensity or the same intensity ratio and each of insulating oils having different degradation degrees can be used to create the correlation relation (master curve) between the ratio K or the difference $\Delta I$ and the insulating oil degradation degree at the transmission of arc discharge light.

As the monochromatic light source having two wavelengths, for example, a halogen lamp that emits white continuous light, a black light, and the like are used, and the irradiation light from them is emitted through the spectroscope, so that the correlation relation can be created.

In addition, of course, the optical fiber 8 including the light reception unit 7 can be disposed to the newly disposed on-load tap changing apparatus 100, but can be easily disposed to the already disposed on-load tap changing apparatus 100. For example, the optical fiber 8 can be easily mounted during maintenance.

It should be noted that due to the difference in oil type and the like, there is the case where the values of the ratios K or the differences $\Delta I$ of insulating oils are different even when they have the same degradation degree. In such a case, the correlation relation (master curve) between the intensity ratio K or the intensity difference $\Delta I$ of arc discharge light that transmits through the insulating oil of each oil type and the insulating oil degradation degree is previously created, so that the accuracy of the degradation degree diagnosis can be improved.

As described above, according to the diagnosing device and the diagnosing method for the on-load tap changing apparatus of this embodiment, the degradation degree of the insulating oil can be easily diagnosed by using the optical measurement technique. In addition, since arc discharge light that occurs in the interior of the apparatus is used as alight source for diagnosis, a separate incident light source is not required, so that the device can be simplified.

Second Embodiment

Figure 5:
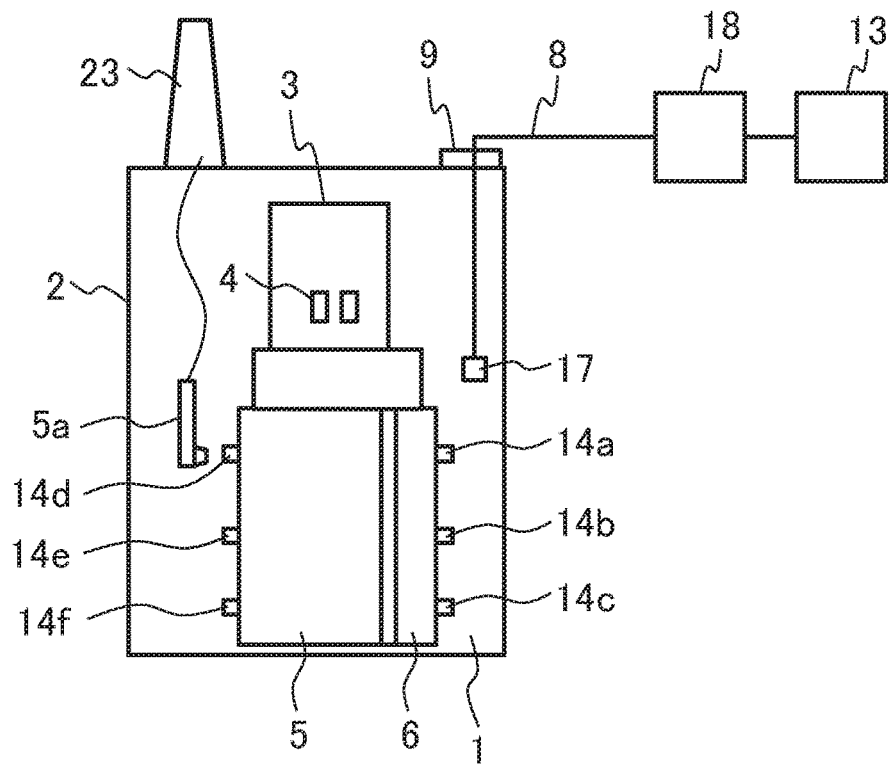
FIG. 5 is a diagram illustrating the overall outline of an on-load tap changing apparatus and a diagnosing device therefor according to an embodiment of the present invention (a second embodiment)

Referring to FIG. 5, the diagnosing device and the diagnosing method for the on-load tap changing apparatus according to a second embodiment will be described. FIG. 5 is a diagram illustrating the overall outline of the on-load tap changing apparatus and the diagnosing device therefor according to this embodiment. It should be noted that hereinafter, portions (configurations) different from the first embodiment will be mainly described.

In this embodiment, the light reception unit 7 for arc discharge light in the first embodiment (FIG. 1) is changed to a color imaging device 17. The image of arc discharge light obtained by the color imaging device 17 is transferred by using the optical fiber 8 through the hermetic terminal 9 mounted on the wall surface of the insulating oil tank 2 of the on-load tap changing apparatus 100, to an image processing unit 18 disposed on the outside of the insulating oil tank 2. The diagnosis result of the degradation degree of the insulating oil 1 that is diagnosed by the image processing unit 18 is displayed on the display unit 13.

Although described in the first embodiment (FIG. 4), with the progression of the degradation of the insulating oil, when arc discharge light transmits through the insulating oil, the peak value of the intensity of the spectral spectrum moves to the short wavelength side. With this movement, the color of the transmission light also changes.

Thus, in this embodiment, for example, the correlation relation (master curve) between the change in the color of the transmission light and the insulating oil degradation degree is created, and is previously stored in the image processing unit 18. Then, the imaging data of the color imaging device 17 is used to be subjected to comparison computation with the master curve stored in the image processing unit 18, so that the degradation degree of the insulating oil 1 can be determined (diagnosed).

It should be noted that like the first embodiment, to create the maser curve, actual arc discharge light and insulating oils having different degradation degrees can be used to determine the correlation relation between the ratio K or the difference $\Delta I$ and the degradation degree of each of the insulating oils. Alternatively, monochromatic light having the two wavelengths $\lambda 1$ and $\lambda 2$ having the same intensity or the same intensity ratio and insulating oils having different degradation degrees can also be used to measure the correlation relation.

As the monochromatic light source having two wavelengths, for example, a halogen lamp that emits white continuous light, a black light, and the like are used, and the irradiation light from them is emitted through the spectroscope, so that the correlation relation can be created.

As described above, in the diagnosing device and the diagnosing method for the on-load tap changing apparatus according to this embodiment, the color imaging device is used to obtain the image data of arc discharge light. Thus, the wavelength detector (detection unit) and the intensity detector (detection unit) are not required, so that the degradation degree of the insulating oil can be diagnosed by a simpler configuration.

Third Embodiment

Figure 6:
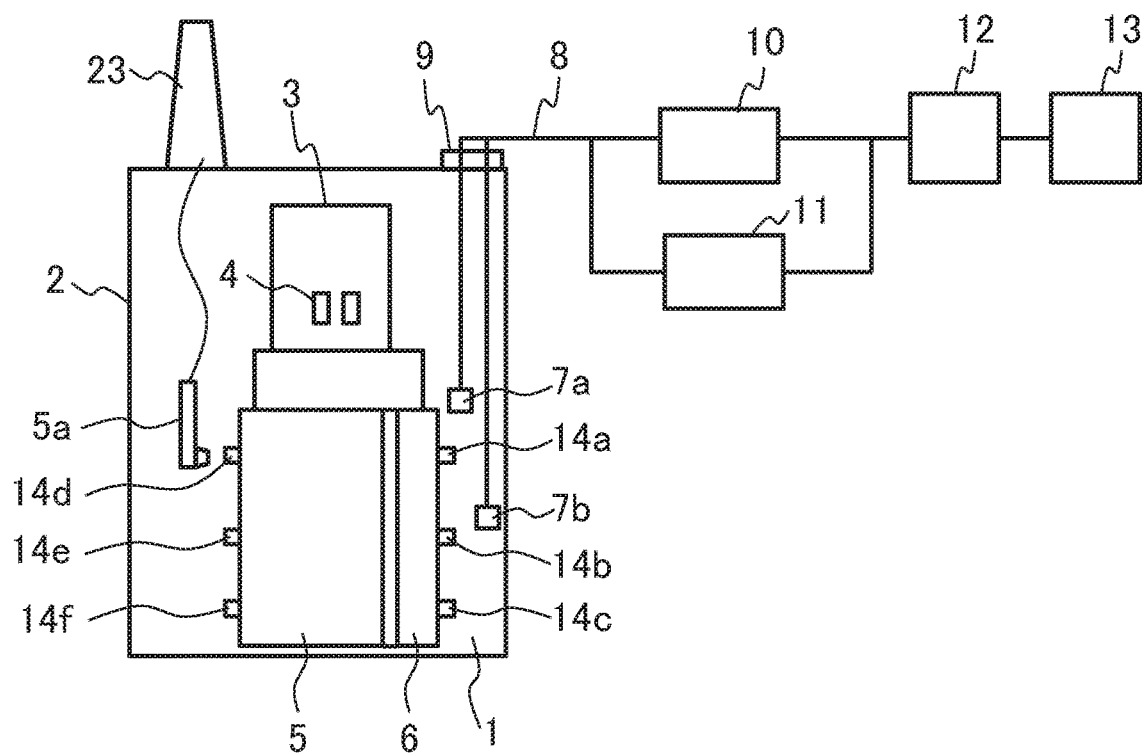
FIG. 6 is a diagram illustrating the overall outline of an on-load tap changing apparatus and a diagnosing device therefor according to an embodiment of the present invention (a third embodiment)

Referring to FIG. 6, the diagnosing device and the diagnosing method for the on-load tap changing apparatus according to a third embodiment will be described. FIG. 6 is a diagram illustrating the overall outline of the on-load tap changing apparatus and the diagnosing device therefor according to this embodiment. It should be noted that hereinafter, portions (configurations) different from the first embodiment will be mainly described.

Since the tap volume is typically relatively large, there is the case where one light reception unit 7 cannot sufficiently receive arc discharge light. Thus, in this embodiment, a plurality of light reception units 7 are disposed in the vicinity of a plurality of tap positions. For example, a light reception unit 7a is disposed in the vicinity of the tap position 14a, and a light reception unit 7b is disposed in the vicinity of the tap position 14b.

As illustrated in FIG. 6, the plurality of light reception units 7 (7a, 7b) are disposed in the vicinity of the plurality of tap positions, so that arc discharge light from any tap can be reliably detected without interception. In addition, even when the light reception unit is disposed in the vicinity of the tap position that is used less frequently due to the electric power use state, it is possible to eliminate the problem of the progressing state of the degradation of the insulating oil being incapable of sufficiently captured (detected) due to the insufficient detection frequency, and the like. Thus, the detection accuracy of arc discharge light can be improved, so that the on-load tap changing apparatus can be diagnosed with higher reliability.

Fourth Embodiment

Figure 7:
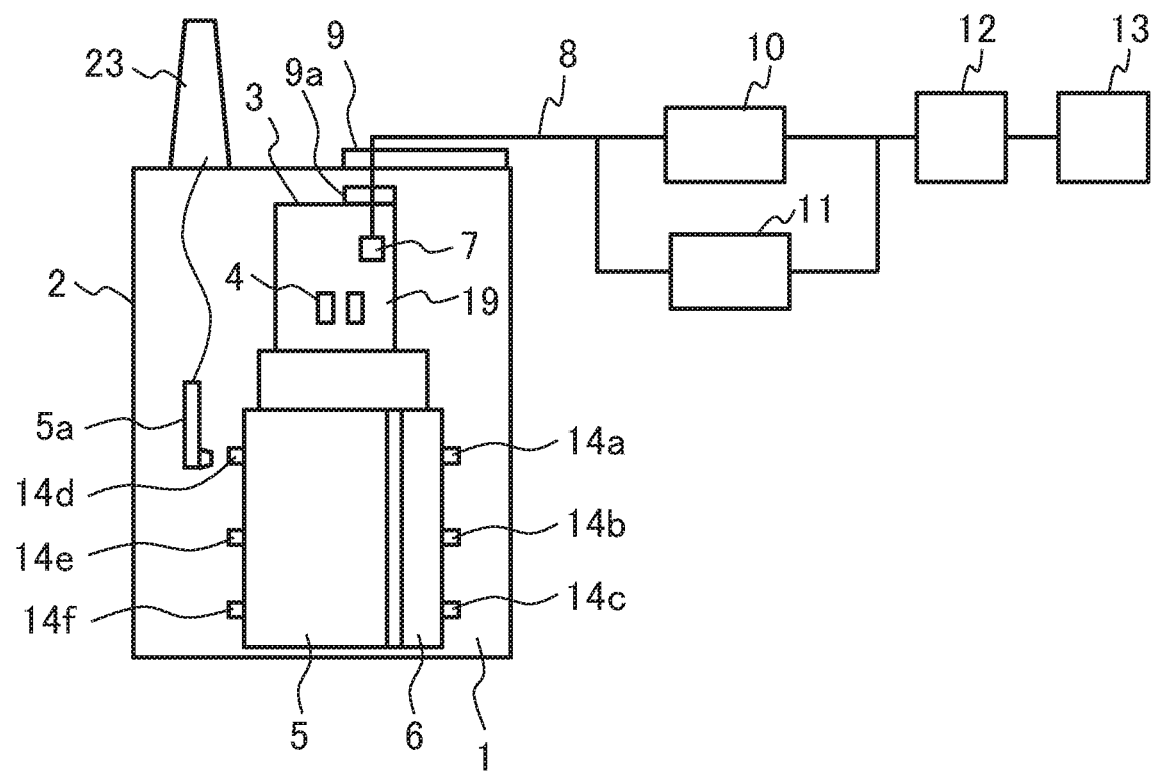
FIG. 7 is a diagram illustrating the overall outline of an on-load tap changing apparatus and a diagnosing device therefor according to an embodiment of the present invention (a fourth embodiment)

Referring to FIG. 7, the diagnosing device and the diagnosing method for the on-load tap changing apparatus according to a fourth embodiment will be described. FIG. 7 is a diagram illustrating the overall outline of the on-load tap changing apparatus and the diagnosing device therefor according to this embodiment. It should be noted that hereinafter, portions (configurations) different from the first embodiment will be mainly described.

Although described in the first embodiment, at the movement of the movable contact of the contact 4 that changes the tap in a state where a load is applied to the changeover switching device 3, that is, during electric conduction, arc discharge occurs between the movable contact and the fixed side contact.

In addition, there is the case where the insulating oil is also sealed within the changeover switching device 3. Thus, as illustrated in FIG. 7, in this embodiment, to diagnose the degradation degree of insulating oil 19 within the changeover switching device 3, the light reception unit 7 is disposed within the oil tank of the changeover switching device 3.

Arc discharge light that is emitted when the contact 4 is opened and closed is received by the light reception unit 7, the signal detected by the light reception unit 7 is transferred by using the optical fiber 8 through a hermetic terminal 9a mounted on the wall surface of the changeover switching device 3 and the hermetic terminal 9 mounted on the wall surface of the insulating oil tank 2 of the on-load tap changing apparatus, to the wavelength detection unit 10 and the intensity detection unit 11 that are disposed on the outside of the insulating oil tank 2 and detect the wavelength and the intensity of the light detected by the light reception unit 7, respectively, and the wavelength signal and the intensity signal are subjected to computation processing by the signal processing unit 12 to diagnose the degradation degree of the insulating oil 19 sealed in the interior of the changeover switching device 3, so that the diagnosis result is displayed on the display unit 13.

It should be noted that like this embodiment (FIG. 7), the light reception unit 7 is disposed within the oil tank of the changeover switching device 3, and besides, like the first embodiment (FIG. 1) and the third embodiment (FIG. 6), needless to say, one or a plurality of light reception units 7 may further be disposed within the insulating oil tank 2 of the on-load tap changing apparatus 100.

In addition, in place of the light reception unit 7, like the second embodiment (FIG. 5), the color imaging device 17 may be disposed within the oil tank of the changeover switching device 3, and the image of arc discharge light obtained by the color imaging device 17 may be diagnosed (image processed) by the image processing unit 18.

As described above, in the diagnosing device and the diagnosing method for the on-load tap switching apparatus according to this embodiment, in addition to the first embodiment, the degradation degree of the insulating oil 19 sealed in the interior of the changeover switching device 3 can be diagnosed.

Fifth Embodiment

Figure 8:
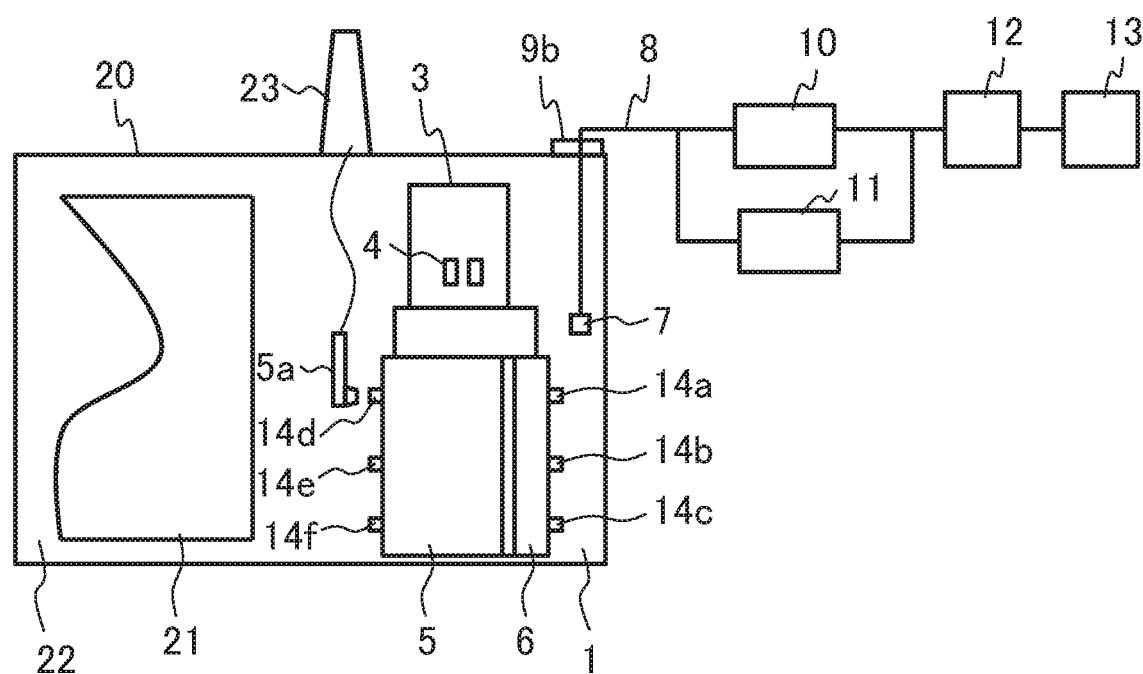
FIG. 8 is a diagram illustrating the overall outline of an on-load tap changing apparatus and a diagnosing device therefor according to an embodiment of the present invention (a fifth embodiment).

Referring to FIG. 8, the diagnosing device for a transformer and the on-load tap changing apparatus and the diagnosing method therefor according to a fifth embodiment will be described. FIG. 8 is a diagram illustrating the overall outline of the transformer, the on-load tap changing apparatus, and the diagnosing device therefor according to this embodiment. It should be noted that hereinafter, portions (configurations) different from the first embodiment will be mainly described.

As illustrated in FIG. 8, there is the case where the on-load tap changing apparatus is disposed on the outside of (in the vicinity of) a winding 21 within a transformer tank 20.

Arc discharge light is emitted when the tap selector 5 or the polarity (transposition) changer 6 selecting the tap of the tap winding, which has been described in the first embodiment, changes the tap position 14, the arc discharge light (optical signal) that transmits through insulating oil 22 sealed in the transformer tank 20 is received by the light reception unit 7, the signal detected by the light reception unit 7 is transferred by using the optical fiber 8 through the hermetic terminal 9 mounted on the wall surface of the transformer tank 20, to the wavelength detection unit 10 and the intensity detection unit 11 that are disposed on the outside of the transformer tank 20 and detect the wavelength and the intensity of the arc discharge light, respectively, and the wavelength signal and the intensity signal of the received light are received and are subjected to computation processing by the signal processing unit 12 to diagnose the degradation degree of the insulating oil 22 sealed in the transformer tank 20, so that the diagnosis result is displayed on the display unit 13.

As described above, in the diagnosing device for the transformer and the on-load tap changing apparatus and the diagnosing method therefor according to this embodiment, in addition to the first embodiment, the degradation degree of the insulating oil 22 sealed in the transformer tank 20 can be diagnosed.

It should be noted that besides the diagnosis of the degradation degree of the insulating oil, the diagnosing device and the diagnosing method which have been described in each of the above-described embodiments are applicable to, for example, the failure diagnosis of the tap selector by the intensity detection of arc discharge light and the detection of arc discharge occurrence time (occurrence continuation time), and the like.

In addition, the present invention is not limited to the above embodiments, and includes various modifications. For example, the wavelength detection unit 10 and the intensity detection unit 11 can also be integrated. In addition, the present invention is also applicable, not only to the detection of the degradation degree of the insulating oil, but also to the detection of the degradation degree of other insulators (gas, resin, and the like). The above embodiments have been described for easily understanding the present invention, and do not necessarily include all the described configurations. In addition, part of the configuration of one embodiment can be replaced with the configurations of other embodiments, and the configuration of one embodiment can be added with the configurations of other embodiments. Further, part of the configuration of each of the embodiments can be subjected to addition, deletion, and replacement with respect to other configurations.

What is claimed is:

1. A diagnosing device for an on-load tap changing apparatus having an insulating oil tank in which insulating oil is sealed, a changeover switching device that is disposed within the insulating oil tank and performs the tap changing operation of a tap winding, a tap selector that selects the tap position of the tap winding, and a polarity (transposition) changer that inverts the polarity of the tap winding or a winding connected to the tap winding,
wherein the diagnosing device includes an arc discharge light detector that detects arc discharge light that is emitted at changing the tap position of the tap selector, and
wherein the degradation degree of the insulating oil is diagnosed based on the arc discharge light detected by the arc discharge light detector.

2. The diagnosing device according to claim 1,
wherein the diagnosing device includes a wavelength detector that detects the wavelength of the arc discharge light detected by the arc discharge light detector, and an intensity detector that detects the intensity of the arc discharge light detected by the arc discharge light detector, and
wherein the degradation degree of the insulating oil is diagnosed based on the wavelength and the intensity of the detected arc discharge light.

3. The diagnosing device according to claim 1,
wherein the arc discharge light detector has a light reception window that is recessed and circular and receives the arc discharge light, the light reception window being disposed opposite the tap position of the tap selector or the polarity (transposition) changer.

4. The diagnosing device according to claim 2,
wherein the wavelength detector selects at least two wavelengths λ1 and λ2 in which the wavelengths of the arc discharge light received by the arc discharge light detector are different from each other, and
wherein the degradation degree of the insulating oil is diagnosed based on the intensity ratio or the intensity difference of the arc discharge light at the wavelengths λ1 and λ2.

5. The diagnosing device according to claim 1,
wherein the arc discharge light detector is a color imaging device that images an image, and
wherein the degradation degree of the insulating oil is diagnosed based on the color information of the image imaged by the color imaging device.

6. The diagnosing device according to claim 1,
wherein a plurality of the arc discharge light detectors are disposed opposite the tap positions of the tap selector or the polarity (transposition) changer.

7. The diagnosing device according to claim 1,
wherein the arc discharge light detector is disposed within the changeover switching device, and
wherein the degradation degree of the insulating oil that is sealed in the interior of the changeover switching device is diagnosed.

8. A diagnosing method for an on-load tap changing apparatus having an insulating oil tank in which insulating oil is sealed, a changeover switching device that is disposed within the insulating oil tank and performs the tap changing operation of a tap winding, a tap selector that selects the tap position of the tap winding, and a polarity (transposition) changer that inverts the polarity of the tap winding or a winding connected to the tap winding,
wherein arc discharge light that is emitted at changing the tap position of the tap selector is received by a light reception unit,
wherein the arc discharge light detected by the light reception unit is transferred through an optical fiber to detection units that are disposed on the outside of the insulating oil tank, and
wherein the arc discharge light is subjected to computation processing by a signal processing unit based on the wavelength and the intensity of the arc discharge light detected by the detection units to diagnose the degradation degree of the insulating oil.

9. The diagnosing method according to claim 8,
wherein at least two wavelengths λ1 and λ2 in which the wavelengths of the arc discharge light received by the light reception unit are different from each other are selected, and
wherein the degradation degree of the insulating oil is diagnosed based on the intensity ratio or the intensity difference of the arc discharge light at the wavelengths λ1 and λ2.

10. The diagnosing method according to claim 9,
wherein the intensity ratio or the intensity difference of the arc discharge light detected by each detection unit and a previously created insulating oil degradation degree correlation relation (master curve) are compared to diagnose the degradation degree of the insulating oil.

11. The diagnosing method according to claim 8,
wherein the degradation degree of the insulating oil is diagnosed based on the color information of the image imaged by the color imaging device.

12. A diagnosing device for a transformer having a transformer tank in which insulating oil is sealed, and an on-load tap changing apparatus that is disposed within the transformer tank,
wherein the on-load tap changing apparatus includes:
a changeover switching device that performs the tap changing operation of a tap winding;
a tap selector that selects the tap position of the tap winding; and
a polarity (transposition) changer that inverts the polarity of the tap winding or a winding connected to the tap winding,
wherein the transformer includes, within the transformer tank, an arc discharge light detector that detects arc discharge light that is emitted at changing the tap position of the tap selector, and
wherein the degradation degree of the insulating oil is diagnosed based on the arc discharge light detected by the arc discharge light detector.

13. The diagnosing device according to claim 12,
wherein the diagnosing device includes a wavelength detector that detects the wavelength of the arc discharge light detected by the arc discharge light detector, and an intensity detector that detects the intensity of the arc discharge light detected by the arc discharge light detector, and
wherein the degradation degree of the insulating oil is diagnosed based on the wavelength and the intensity of the detected arc discharge light.

14. The diagnosing device according to claim 12,
wherein the arc discharge light detector has a light reception window that is recessed and circular and receives the arc discharge light, the light reception window being disposed opposite the tap position of the tap selector or the polarity (transposition) changer.

15. The diagnosing device according to claim 13,
wherein the wavelength detector selects at least two wavelengths $\lambda 1$ and $\lambda 2$ in which the wavelengths of the arc discharge light received by the arc discharge light detector are different from each other, and
wherein the degradation degree of the insulating oil is diagnosed based on the intensity ratio or the intensity difference of the arc discharge light at the wavelengths $\lambda 1$ and $\lambda 2$.

16. The diagnosing device according to claim 12,
wherein the arc discharge light detector is a color imaging device that images an image, and
wherein the degradation degree of the insulating oil is diagnosed based on the color information of the image imaged by the color imaging device.

17. The diagnosing device according to claim 12,
wherein a plurality of the arc discharge light detectors are disposed opposite the tap positions of the tap selector or the polarity (transposition) changer.

18. The diagnosing device according to claim 12,
wherein the arc discharge light detector is disposed within the changeover switching device, and
wherein the degradation degree of the insulating oil that is sealed in the interior of the changeover switching device is diagnosed.

* * * * *